United States Patent
Geier

[11] Patent Number: 5,284,132
[45] Date of Patent: Feb. 8, 1994

[54] DEVICE FOR THE TRANSNASAL OR ORAL ADMINISTRATION OF DRUGS OR THE LIKE

[75] Inventor: Adalbert Geier, Villazzano, Italy

[73] Assignee: Coster Technologie Speciali S.p.A., Mailand, Italy

[21] Appl. No.: 682,464

[22] Filed: Apr. 9, 1991

[30] Foreign Application Priority Data

Apr. 17, 1990 [DE] Fed. Rep. of Germany ....... 4012270
May 18, 1990 [DE] Fed. Rep. of Germany ....... 4016126

[51] Int. Cl.$^5$ ................ A61M 11/00; A61M 15/08; A61M 5/315
[52] U.S. Cl. ................ 128/200.22; 128/203.23; 128/203.22; 604/237; 604/224; 604/94
[58] Field of Search ........ 128/200.14, 200.21, 128/200.22, 203.21, 203.23, 203.24, 203.12; 604/26, 71, 131, 133, 181, 218, 224, 228, 236, 237, 94

[56] References Cited

U.S. PATENT DOCUMENTS

| | | | |
|---|---|---|---|
| 594,721 | 11/1897 | Bengué | 128/200.14 |
| 606,240 | 6/1898 | Prescott | 128/200.22 |
| 713,017 | 11/1902 | Pumphrey | 128/200.14 |
| 1,301,149 | 4/1919 | Marshall | 128/200.22 |
| 2,191,015 | 2/1940 | Hoffman | 128/203.23 |
| 2,485,184 | 10/1949 | Blackman et al. | 128/200.22 |
| 2,585,429 | 2/1952 | Boe | 128/200.23 |
| 2,667,166 | 1/1954 | Scheer | 128/200.14 |
| 2,785,768 | 3/1957 | Gauchard | 128/200.14 |
| 3,848,773 | 11/1974 | Adler et al. | 128/203.21 |
| 4,961,727 | 10/1990 | Beard | 128/200.22 |
| 4,962,868 | 10/1990 | Borchard | 128/200.14 |
| 5,020,527 | 6/1991 | Dessertine | 128/200.14 |
| 5,042,467 | 8/1991 | Foley | 128/200.14 |
| 5,056,511 | 10/1991 | Ronge | 128/200.14 |

FOREIGN PATENT DOCUMENTS

| | | | |
|---|---|---|---|
| 777286 | 2/1935 | France | 128/200.21 |
| 2625981 | 7/1989 | France | |
| 2635084 | 2/1990 | France | |
| 376096 | 7/1973 | U.S.S.R. | 128/200.22 |

Primary Examiner—Edgar S. Burr
Assistant Examiner—Kimberly L. Asher
Attorney, Agent, or Firm—Andrus, Sceales, Starke & Sawall

[57] ABSTRACT

A device for the transnasal or oral administration of drugs or similar media, comprising a finger-like applicator (3) which has a spray nozzle (6) disposed at its free end and includes a cylinder unit (1) for accommodating the medium to be administered. The medium is applied by moving a piston (7) into the cylinder unit (1). A membrane-like seal (4) is located between the cylinder unit and spray nozzle and is slotted to open and form a fluid passage under pressure. The cylinder unit may be built into the applicator or may include a separate cartridge releasably mounted in the applicator. The piston may be activated in steps or in a continuous motion. A second applicator may be attached to the side of the first applicator with the spray nozzles located generally in accordance with spacing of human nose nostrils.

13 Claims, 6 Drawing Sheets

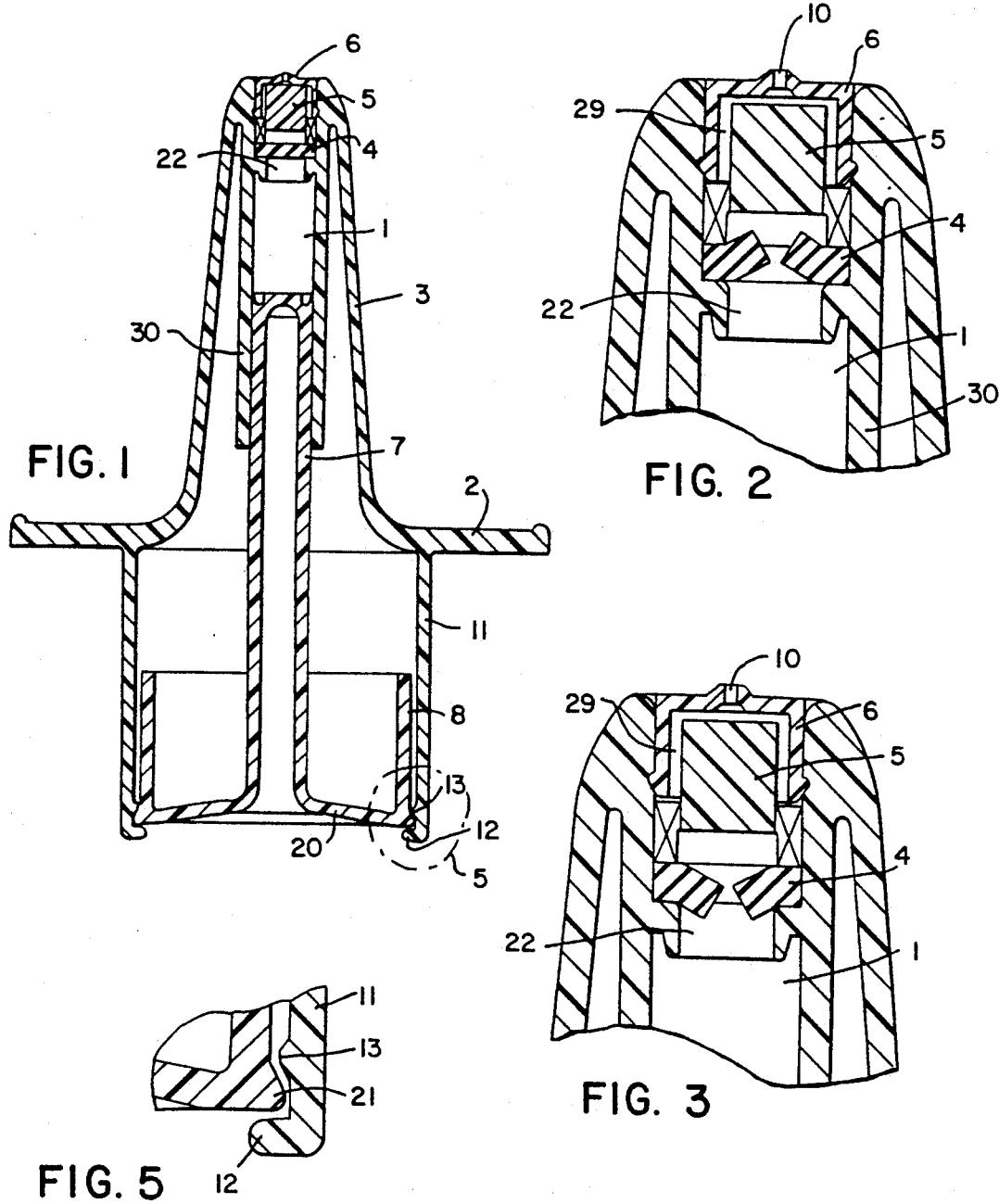
FIG. 1
FIG. 2
FIG. 3
FIG. 5
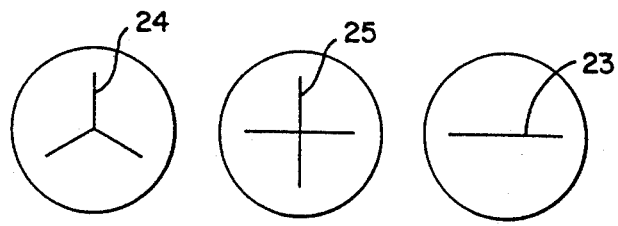
FIG. 4

DEVICE FOR THE TRANSNASAL OR ORAL ADMINISTRATION OF DRUGS OR THE LIKE

BACKGROUND OF THE INVENTION

The invention is concerned with a device for the transnasal or oral administration of drugs or similar media.

A device of the specified kind is known. It was developed with a view to the fact that the nasal mucous membrane or the throat are ideal areas of application for drugs. The technical design of such devices is subject to the most stringent requirements, because the question as to what drugs may be used in this way is governed by the dosing accuracy. Moreover, it is essential that handling should be convenient to the user. These two prerequisites must be satisfied so as to ensure a sufficiently high operativeness which is of the utmost importance for the application of highly effective drugs.

One of the problems arising with the known devices is the risk of contamination. No device-integrated measures have been provided to ensure that the content does not come into contact with air and hence with the environment.

Also, there is a basic risk of leakage when the spray nozzle is improperly closed. Finally, the known device is composed of a relatively large number of parts, resulting in a correspondingly high expense in respect of manufacture, material and assembly time, whereby the mechanical operativeness may also be deteriorated.

The present invention is based on the object of providing a device of the kind specified above, which is of simple structure while it is highly reliable in operation and safe from contamination.

SUMMARY OF THE PRESENT INVENTION

In accordance with the invention the specified object is solved by a device including a finger-like applicator having a spray nozzle at its outer or free end. The applicator includes a cylinder unit for receiving the fluid medium to be administered. A piston in the cylinder unit is operable to force the medium through the spray nozzle. In accordance with the present invention, a membrane-like seal member is located within the applicator and closes the passageway to the spray nozzle for the cylinder unit. The membrane-like seal member has a releasable fluid passage which opens under pressure and is provided upstream of the spray nozzle. The membrane seal member is fixed as by clamping it along its peripheral edge within the applicator, with the passage formed by slits in the membrane.

In one embodiment, the structure permits multiple application with a predetermined dosage of a liquid mixed with drugs. Hence, the present concept of the invention may provide for a single-dosage or multiple-dosage applicator.

The membrane-like seal which is provided in accordance with the invention between spray nozzle and the pump or cylindrical unit containing the medium to be administered permits secure permanent sealing of the drug-containing fluid charge with respect to the environment. The membrane-like seal opens and forms a fluid passage only for purposes of charging and/or administering the fluid medium.

The above-mentioned membrane seal is a device-integrated component which is no longer accessible after assembly and therefore cannot be manipulated. It is preferred to dispose the membrane seal in a passage between cylinder space and spray nozzle with the membrane seal fixedly clamped along its peripheral edge. In accordance with one embodiment of the invention, clamping is effected by means of an adapter member which is disposed between the membrane seal and the spray nozzle and has the additional function of distributing the administered medium prior to its exit from the spray nozzle; preferably, the side of the adapter which faces the spray nozzle is also provided with a structure for swirling the medium exiting through the spray nozzle.

For the purpose of defining a fluid passage through the membrane seal the latter is formed with a straight, a star-shaped or a cross-recessed slot which opens upon application of a predetermined pressure towards the outside in case of application and towards the inside when the device is charged, i.e. in the direction towards the pump or cylinder space which accommodates the medium to be administered.

The piston cooperating with the above-mentioned cylinder space is preferably held in the initial position by a locking mechanism adapted to be overcome for applying pressure to a piston actuating surface formed at the end of the piston remote from the spray nozzle. The piston is adapted to be moved continuously or stepwise into the cylinder space while performing a single or multiple-application of the fluid medium.

In one embodiment, a charging cartridge is inserted in the chamber as a component separate from the applicator mechanism so that the latter is suited for multiple use.

Special structure is disclosed and claimed for the various devices described above as well as particulars of the preferred embodiments.

BRIEF DESCRIPTION OF THE DRAWINGS

Below, two embodiments of a device in accordance with the present invention will be described in detail with reference to the accompanying drawings, in which:

FIG. 1 is a longitudinal section of a device according to the present invention;

FIG. 2 is an enlarged longitudinal section of the sprayer portion of the device shown in FIG. 1, illustrating the membrane seal of the invention during application;

FIG. 3 is an enlarged longitudinal section of the sprayer portion shown in FIG. 2, illustrating the membrane seal of the invention during charging of the device;

FIG. 4 shows the plan views of three different embodiments of the membrane seal used in accordance with the invention;

FIG. 5 is an enlarged view of a detail V in FIG. 1;

DESCRIPTION OF THE ILLUSTRATED EMBODIMENT

Figure 6:
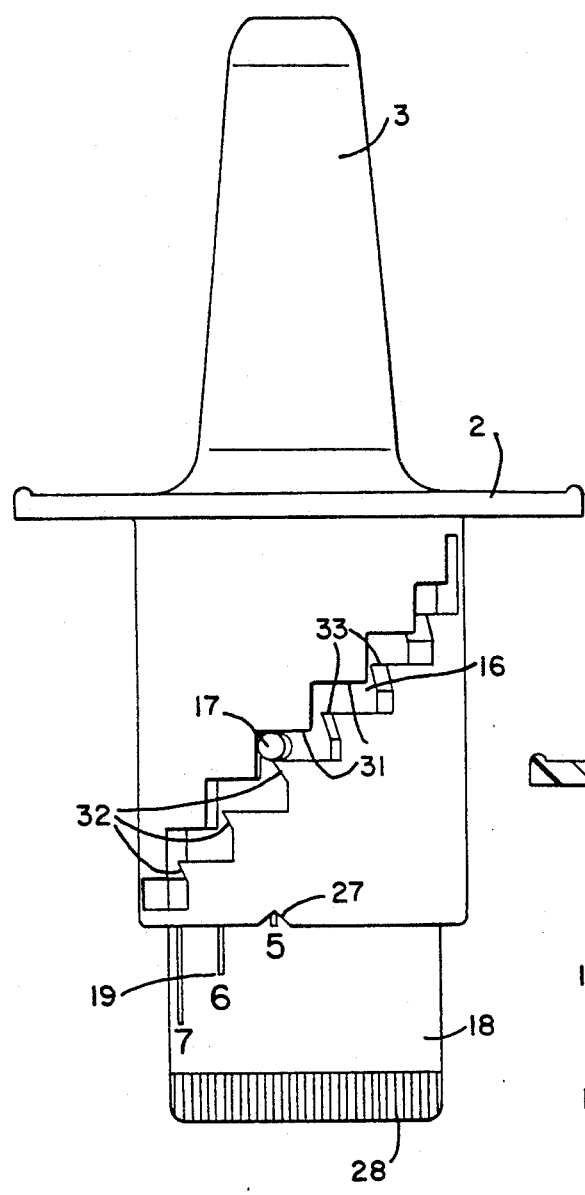
FIG. 6 is a side view of a second embodiment of the device in accordance with the invention.

The device shown in FIG. 1 for the transnasal or oral administration of drugs or similar media, especially fluid media, comprises a tubular or finger-like applicator 3 having a spray nozzle 6 disposed at the free end thereof. The interior of the applicator 3 comprises a cylinder space 1 extending in the longitudinal direction of the applicator for accommodating the medium to be administered, said medium being administered by means of a piston 7 from the cylinder space 1 through the spray nozzle 6. At the upstream end of the spray nozzle 6 a membrane-like seal 4 is disposed having a fluid passage which opens under pressure. The membrane seal 4 is made from a highly elastic material, preferably plastic material, rubber or synthetic rubber. The applicator 3 including the cylinder 1 and the piston 7 likewise are preferably made from plastic material. As will be apparent especially from FIGS. 2 and 3, the membrane seal 4 is disposed in a through-hole 22 between cylinder space 1 and spray nozzle 6 and is fixedly clamped along its peripheral edge. Clamping of the membrane seal 4 is effected by an intermediate or adapter member 5 which is disposed between the membrane seal and the spray nozzle 6 and which at the same time is used to distribute the administered medium prior to exiting of the same through the spray nozzle 6; the side of the adapter member 5 which faces the spray nozzle 6 has swirling means provided thereon for swirling the medium exiting from the spray nozzle 6. The specified means is defined by a plurality of swirl ducts formed at the specified location.

The afore-mentioned fluid opening in the membrane seal 4 is defined either by a straight slot 23, a star-shaped slot 24 or a cross-recessed slot 25. Plan views of these three alternatives are illustrated in FIG. 4. In the initial state the content of the pump or cylinder space 1 is hermetically sealed by the piston 7 on the downward side and by the seal 4 on the upward side. It is only upon actuation of the piston 7 and the resulting development of pressure within the cylinder space 1 that the membrane seal 4 will be elastically deformed outwardly or towards the spray nozzle 6 so that the aforementioned slot 23, 24 or 25 clears a fluid opening. This condition is illustrated in FIG. 2. By the way, it is also apparent from FIG. 2 that the spray nozzle 6 is formed by a cup-like member the bottom of which is formed with a microaperture 10 through which the administered medium is atomized An annular gap is defined between the inside of the sidewall of the afore-mentioned cup-like sprayer member and the adapter member 5 through which gap the medium to be administered flows both during administering and during charging of the cylinder space 1 while being equally distributed about the circumference. The mentioned annular space is indicated at 29 in FIGS. 2 and 3.

To clear the path through the membrane seal 4 to the outside it is necessary to exert more or less power depending on the elasticity and thickness of the seal 4. This results in an advantageous development of pressure which is required for good atomization of the administered medium through the spray nozzle 6 and its micro-aperture 10.

FIG. 3 is a view of the sprayer part similar to FIG. 2, the difference residing in that FIG. 3 illustrates the deformation of the membrane seal 4 when the cylinder space 1 is charged with the medium to be administered. The charging head, which is not illustrated in detail, is configured so that prior to charging of the cylinder space 1 air is initially exhausted through the spray nozzle 6 or the microaperture 10 thereof. Only then charging with the medium to be administered actually takes place. After removal of the charging head the membrane seal 4 closes automatically so that no air is entrapped in the cylinder space 1 after charging. The charged medium has a correspondingly long storage stability. The instant device is supplied in charged state. In this condition the piston 7 has the initial position illustrated in FIG. 1. It is held in this position by a locking mechanism which for purposes of administration must be overcome by the application of pressure to a piston actuating surface 20 defined at the end of the piston 7 remote from the spray nozzle 6. In the illustrated embodiment, the piston actuating surface 20 is part of a cylinder cup 8 which is open towards the spray nozzle 6 and extends coaxially with the piston 7 and is movably guided within a guide cylinder 11 connected to the finger-like applicator 3. The locking mechanism is defined on the one hand by a protrusion, i.e. an annular protrusion 21 formed on the cylinder cup 8 and, on the other hand, by a complementary recess, i.e. an annular groove formed by the elements 12, 13 formed on the inside of the guide cylinder 11 as most clearly shown in FIG. 5. The delimitation of the annular groove by elements 12 and formed on the inside of the guide cylinder 11, which delimitation is remote from the spray nozzle 6 and particularly element 12, at the same time serves as a stop member preventing withdrawal of the piston 7 from the cylinder space 1 of the applicator 3. In the illustrated embodiment the stop member element 12 is formed by turning the free peripheral edge of the guide cylinder 11 inwardly. The guide cylinder 11 is integrally formed with the applicator 3 and the cylindrical wall 30 defining the cylinder space 1. The same applies to the piston 7 and its actuating portion 8, 20. FIG. 5 illustrates the above-mentioned locking mechanism in even more detail.

The above-described embodiment is used for single application.

Figure 7:
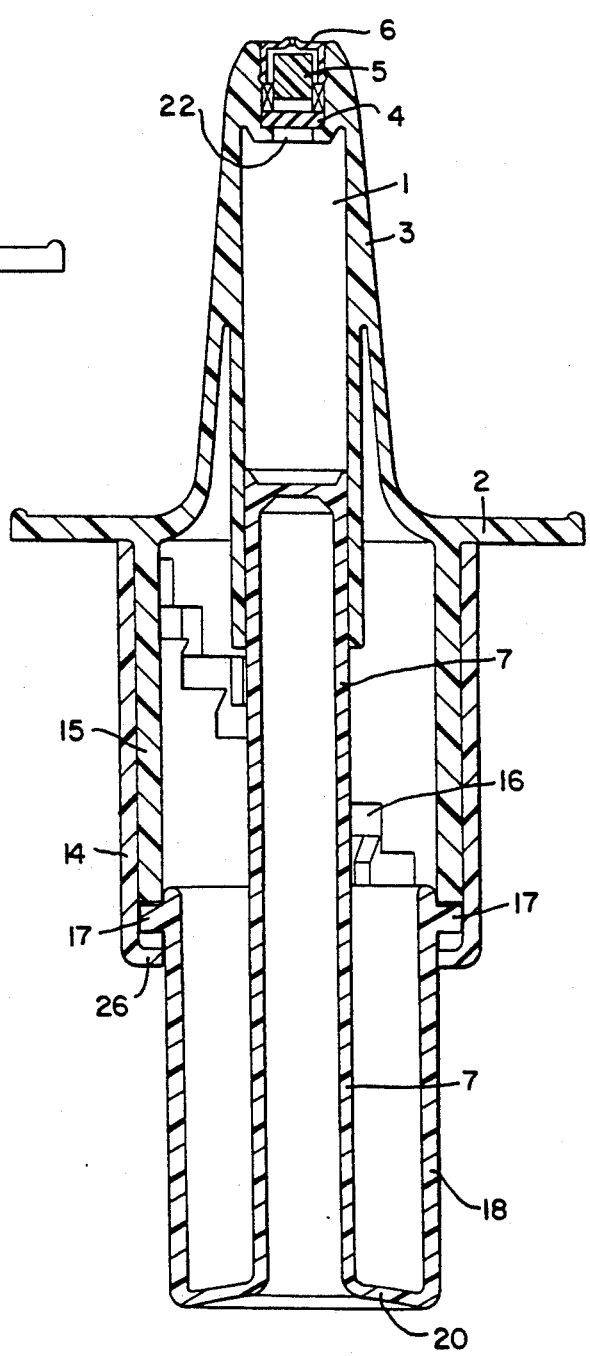
FIG. 7 is a longitudinal section of the device shown in FIG. 6 with, however, the applicator piston still in the initial position.

FIGS. 6 and 7 illustrate a device which permits multiple application. All of the structural features already described with reference to FIGS. 1 to 5 are indicated by the same reference characters in FIGS. 6 and 7. In this respect reference shall be made to the previous description of these features.

The device illustrated in FIGS. 6 and 7 is distinguished by the fact that the piston 7 is adapted to be moved in stepwise fashion into the cylinder space 1 while a corresponding multiple application takes place, and to this end a piston actuating surface 20 is likewise defined at the end of the piston 7 remote from the spray nozzle 6. As in the previous embodiment, the piston actuating surface 20 is part of a cylinder cup 18 which is open towards the spray nozzle 6 and extends coaxially with the piston 7 and is movably guided within a guide cylinder 15 connected to the finger-like applicator 3; on the cylinder cup 18 two diametrically opposed, radially extending pin-like projections 17 are formed each of which engages in stepped guide means 16 defined on the guide cylinder 15. By turning and moving the piston 7 relative to the guide cylinder 15 a respective guide step 31 can be overcome while a dose which is predetermined by the axial extent of the guide step is correspondingly applied. In the instant case the stepped guide means 16 is respectively configured as a hole through the cylinder wall. An outer cover cylinder is fitted on the guide cylinder 15 which is integrally joined with the applicator 3, the peripheral edge 26 of the cover cylinder which is remote from the spray nozzle 6 being bent inwards to form a stop member preventing inadvertent withdrawal of the piston 7 from its cylinder space 1.

As illustrated in FIG. 6, the peripheral edge 26 of the outer cover cylinder 14 remote from the spray nozzle 6 is provided with a marking, i.e. a marking notch 27 which corresponds to a marking, i.e. division marks 19 on the outer surface of the cylinder cup 18 comprising the finger-actuated surface 20, the circumferential spacing between the last-mentioned division marks 19 corresponding to the circumferential pitch of the stepped guide means 16 formed on the inner guide cylinder 15 or, respectively, to the circumferential spacing between adjacent guide steps 31 of the afore-mentioned stepped guide means 16. To facilitate turning of the member 18 it is provided with a knurled portion 28 at its free periphery which extends towards the outside. Hence, for multiple administration of a predetermined dose the member 18 must initially be turned anti-clockwise within one step 31 until the projections 17 engage the vertical portions of the respective step 31. Then, the piston 7 can be pushed into the cylinder space 1 while a dose of the drug is correspondingly administered until the pins 17 abut the upper delimitation of the nextfollowing step of the stepped guide means 16.

In all of the embodiments of the invention radially projecting webs or a radially projecting flange 2 are/is formed at the foot or root or end of the finger-like applicator 3 remote from the spray nozzle 6, said webs or said flange being used to support the user's index and middle fingers upon actuation of the piston 7 by causing the thumb to apply pressure against the piston actuating surface 20 cooperating with the piston 7. The finger-like applicator 3 is disposed between index and middle finger.

To prevent any return movement of the piston 7 by the user, every guide step 31 preferably cooperates with a detent member which after passage of the pins 18 blocks any return movement. Such a detent member may, for instance, be configured as a detent wedge with an elastically compliant ramp face across which the pin 17 may be moved. Any return movement is blocked by a stop face of the detent wedge extending perpendicularly to the direction of movement of the pins 17. The afore-mentioned ramp face is indicated at 32 while the afore-mentioned stop face is indicated at 33 in FIG. 6. The detent wedge defined by the faces 32, 33 is respectively provided in the axially extending guide portion of the guide steps 31 in such a way that the stop face is at the level of the lower delimitation of each guide step 31.

Leaf spring-like detent tabs or the like may also be used as detent members. It is, however, preferred that the detent members should act to prevent any axial return movement of the piston. A return rotation of the piston within a guide step is not critical.

A third embodiment of the device according to the invention is illustrated in FIGS. 8 to 10, and again all structural features which have already been described previously are indicated by the same reference characters in FIGS. 8 to 10. Reference shall be made to the previous description of these features.

Figure 8:
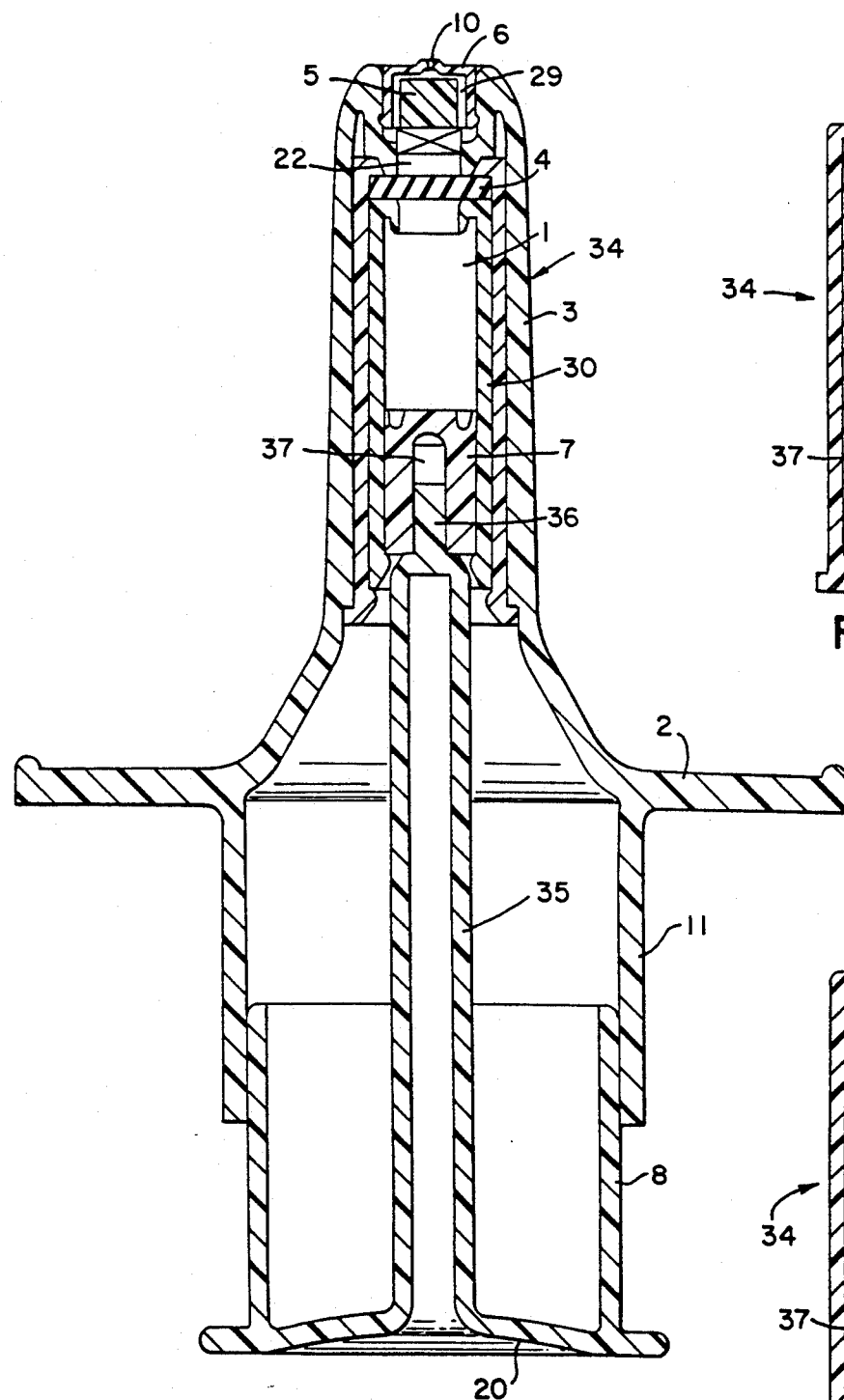
FIG. 8 is a longitudinal section showing a third embodiment of the device according to the invention.
Figure 9:
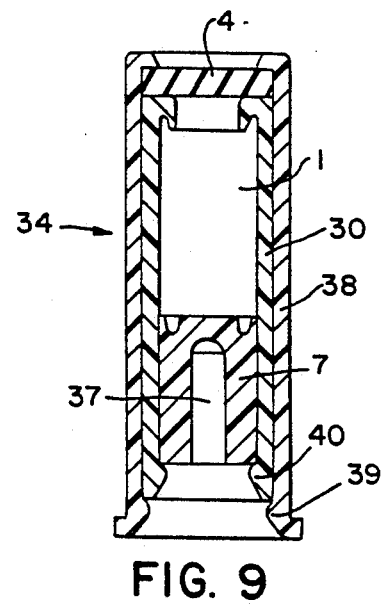
FIG. 9 is a longitudinal section of the charging cartridge which is part of the device shown in FIG. 8.
Figure 10:
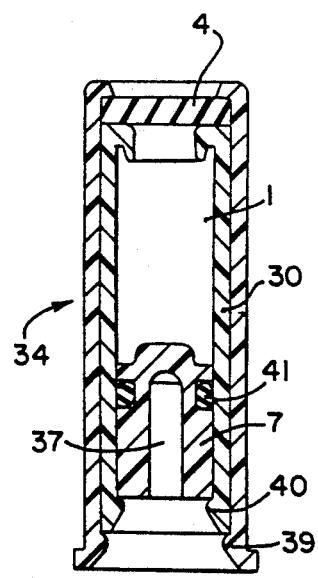
FIG. 10 is another longitudinal section of a charging cartridge which is a modification of FIG. 9.
Figure 11:
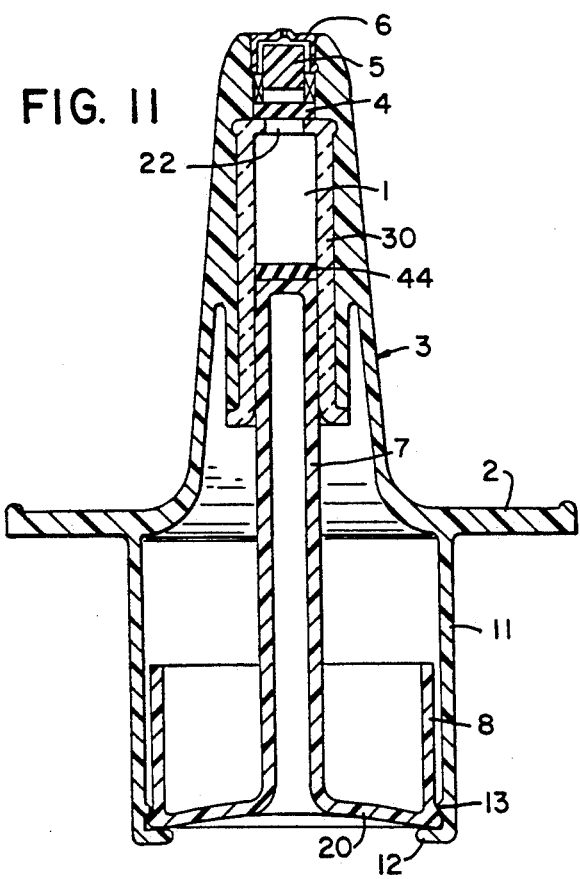
FIG. 11 to 14 is a fourth embodiment of a device according to the invention similar to the illustrations of FIGS. 1, 2 and 3, in which a glass cylinder employed in this embodiment is additionally shown (FIG. 12)
Figure 12:
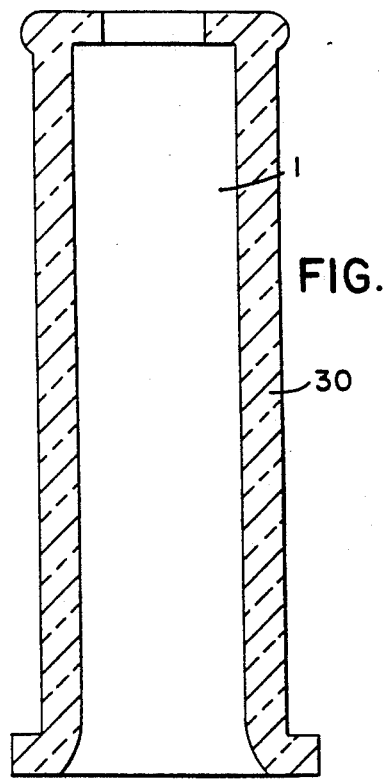
Figure 13:
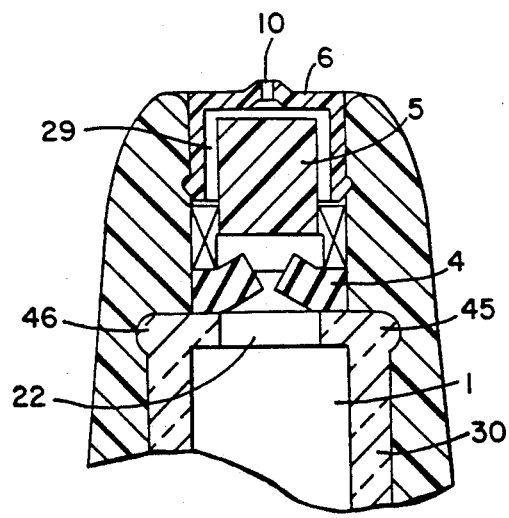
Figure 14:
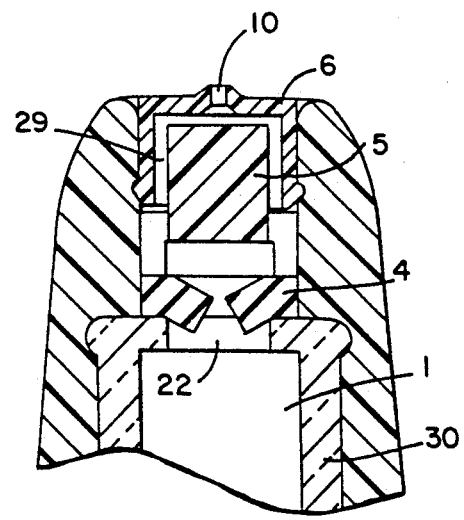

The device shown in FIGS. 8 to 10 is distinguished by the fact that the cylinder space 1 is defined by a separate cartridge which can be positioned in the applicator 3 prior to operation of the device, as illustrated in FIG. 8. The aforementioned cartridge 34 which defines the cylinder space 1 is delimited on the side facing the spray nozzle 6 by the membrane-like seal 4 while the opposite side is delimited by the piston 7. The piston 7 forms part of the cartridge 34, i.e. it is separate from the piston actuating element. The piston actuating element is defined by a plunger 35 formed on the end of the piston actuating surface 20 remote from the piston 7. The connection between piston 7 and plunger 35 is through a pin 36 arranged on the piston-side end of the plunger 35 for insertion in a corresponding axial bore 37 of the piston 7 (see FIG. 8). As illustrated in FIGS. 9 and 10, the cartridge 34 comprises an inner cylinder sleeve 30 which laterally defines the cylinder space 1 and inside which the piston 7 is movably mounted, and an outer cylinder sleeve 38 which is fitted or slid over the inner cylinder sleeve 30 whereby the membrane seal 4 is fixed between the spray nozzle-side periphery of the inner cylinder sleeve 30 and the spray nozzle-side periphery of the outer cylinder sleeve 38. In the assembled state the two cylinder sleeves 30, 38 are locked to each other (locking protrusion 39). At the peripheral edge of the inner cylinder sleeve 30 remote from the spray nozzle there is formed a radially inwardly extending annular protrusion 40 for preventing the piston 7 from slipping off the inner cylinder sleeve 30.

The cartridge 34 shown in FIG. 10 differs from that shown in FIG. 9 only in that the piston 7 is provided with an annular piston sealing ring 41 which corresponds to the inside of the inner cylinder sleeve 30. It is preferred that the sealing ring 41 is an O-ring and is made of rubber or a similar material.

The embodiment illustrated in FIGS. 8 to 10 offers the advantage that the actuating mechanism of the applicator may be used a number of times. It is merely required to replace the cartridge 34, i.e. the empty cartridge, by a cartridge charged with the active medium. To this end one merely withdraws the piston actuating element 8, 20, 35 from the guide cylinder 11 while the cartridge 34 is withdrawn concurrently. Thereafter, the plunger 35 is removed from the corresponding bore 37 in the piston. Subsequently, a fresh cartridge 34 is inserted into the applicator 3 and is joined to the plunger 35 via the pin 36. The corresponding pin connection is not absolutely necessary, but it is advantageous or suitable for the afore-mentioned reason, i.e. for the purpose of replacing the cartridge.

In all other respects the operation of the above-described applicator is comparable with the operation of the applicator illustrated in FIGS. 1 to 5 or 6 and 7, respectively.

The embodiment illustrated in FIGS. 11 to 14 differs from that of FIGS. 1 to 4 only in that the cylinder space 1 is defined by a separate cylinder sleeve 30 made of glass or a similar impermeable material, said cylinder sleeve being fixed within the applicator finger by a locking fit (locking groove 45/locking protrusion 46) while the membrane-like seal 4 is simultaneously clamped.

Furthermore, the above-described embodiment is distinguished by the fact that a disk-like piston seal 44 is in engagement with, i.e. rests loosely on, the piston face of the piston 7. Thus, the piston seal 44 is not fixed to the piston 7. Nevertheless, the piston seal is fully operative because on charging of the cylinder space 1 it is pushed together with the piston 7 in a direction leading out of the cylinder space 1. Reversely, it is moved together with the piston 7 when the latter is actuated. Hence, due to the overpressures prevailing within the cylinder space 1 both during charging and during application the piston seal 44 is always held in engagement with the face of the piston 7.

Figure 15:
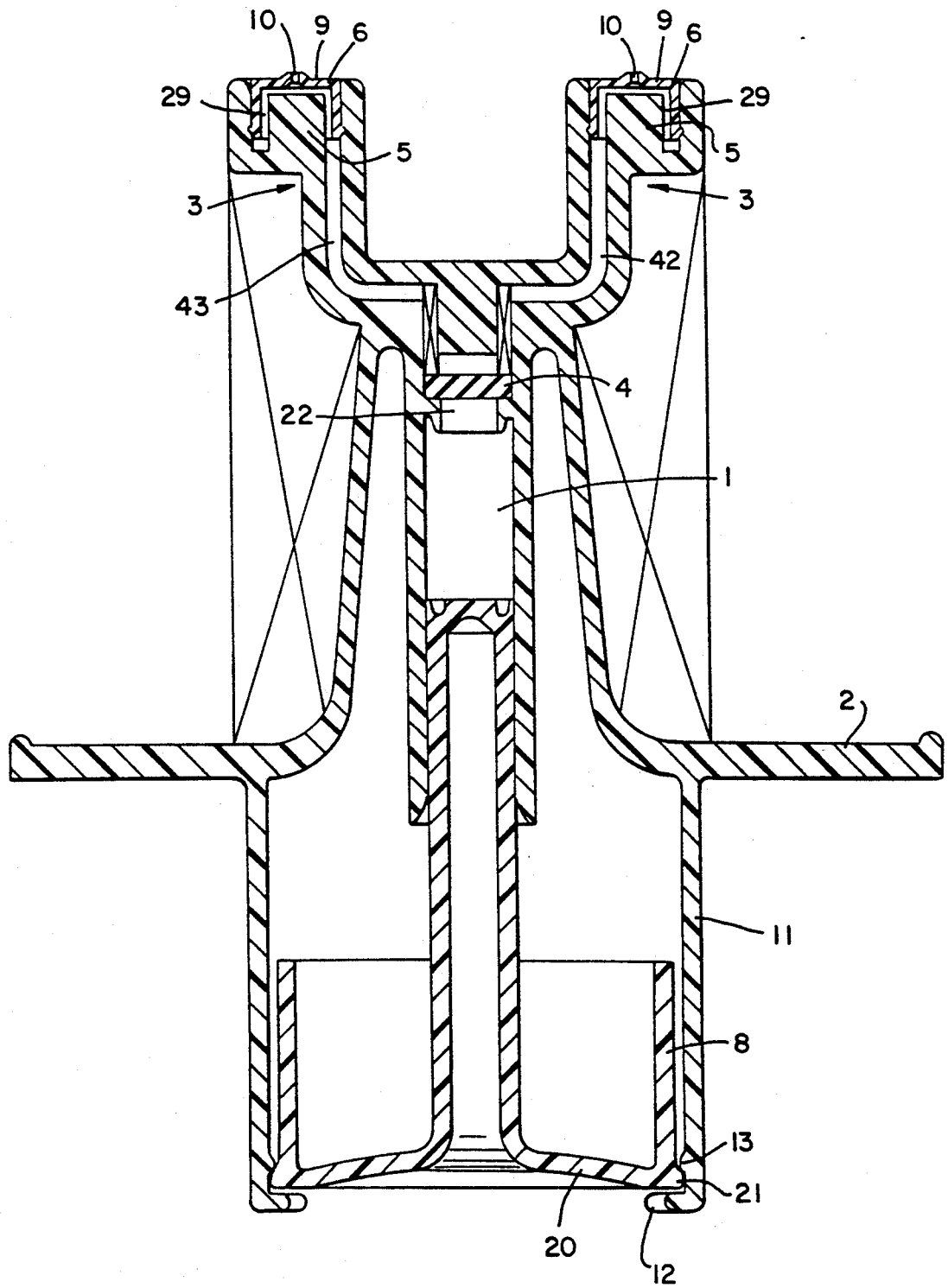
FIG. 15 is a longitudinal section of a dual-applicator device according to the invention.
Figure 16:
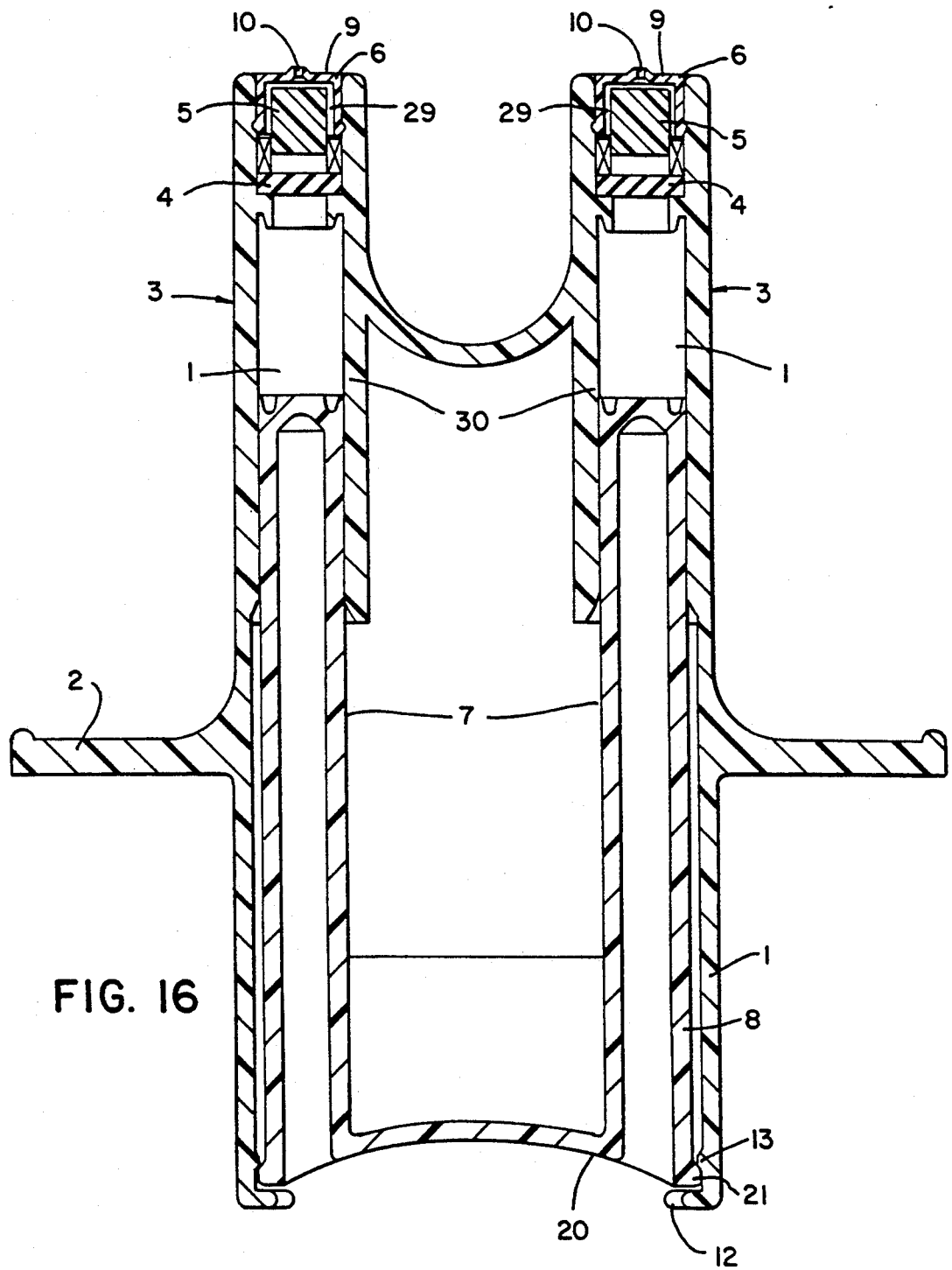
FIG. 16 is a modification of the embodiment illustrated in FIG. 15.

The embodiments illustrated in FIGS. 15 and 16 are distinguished in that each comprises two jointly operated applicators 3 which are disposed at such a distance from each other that the medium to be administered may be sprayed concurrently into both nostrils of the user. In the embodiment shown in FIG. 16, every applicator 3 cooperates with a separate piston-and-cylinder unit of the afore-described kind, in this case of the kind described with reference to FIGS. 1 to 5, both pistons 7 being connected to each other through a common piston actuating surface 20. Accordingly, both pistons 7 can be actuated jointly. This means that the same dose of remedy is administered through either of the spray nozzles 6.

The embodiment shown in FIG. 15 is characterized in that both applicators 3 cooperate with a common piston-and-cylinder unit of the afore-described kind, wherein the cylinder space 1 is in fluid communication with the spray nozzles 6 of either applicator 3 via two fluid passages 42 and 43 which are each defined downstream of the membrane-like seal 4. In respect of operativeness the embodiment shown in FIG. 15 corresponds to that shown in FIG. 16. The two embodiments differ merely in respect of the cylinder content.

All of the features disclosed in the present application papers are claimed as being essential to the invention provided they are novel either individually or in combination over the prior art.

I claim:

1. A device for the administration of fluid drugs or similar fluid media to a patient by a human operator, comprising a finger-like applicator (3) having a spray nozzle (6) disposed at the free end thereof and a cylinder unit (1) for accommodating the media to be administered, a piston (7) having an inner end located within the cylinder unit and having an outer actuating end (20) projecting from the cylinder unit, said outer actuating end engagable by the fingers of the human operator for movement of said inner end through the cylinder unit (1) and forcing the media through the spray nozzle (6), the improvement comprising a substantially flat membrane seal (4) located between the cylinder unit and the spray nozzle, said membrane seal having an outer peripheral edge secured to said cylinder unit and spray nozzle having a central flexible portion having a first side exposed to the cylinder unit and a second side exposed to the spray nozzle, said central flexible portion including at least one slot portion forming a normally closed fluid passage, said flexible portion of said membrane seal being deflected adjacent said slot in response to a selected pressure applied to said membrane seal to open said fluid passage, said first and second sides of said central flexible portion of said membrane seal being unsupported and free to deflect toward said cylinder unit or toward said spray nozzle, said selected pressure generated by movement of said piston by the operator forcing said media from the cylinder unit and deflecting said flexible portion to open said slot portion of said membrane seal and transfer the media into the spray nozzle (6), means for coupling and loading said nozzle and said cylinder unit with pressurized source of said media, said selective pressure deflecting said flexible portion toward said cylinder unit to open said slot and transfer media into said cylinder unit from said pressurized source of said media.

2. The device of claim 1, having a transfer passage (22) between said cylinder unit (1) and said spray nozzle (6) and wherein said membrane seal (4) is disposed in said passage (22) between said cylinder unit (1) and the spray nozzle (6), and a clamp unit securing said peripheral edge of said membrane seal to said transfer passage, and said slot portion being located generally centrally of said transfer passage.

3. The device of claim 1, wherein said piston has an initial position in said cylinder unit (1) with said actuating end remote from the spray nozzle (6) for moving said piston, a releasable locking mechanism connected to the piston (7) for holding the piston in the initial position, said locking mechanism released in response to a release pressure on the piston actuating end (20).

4. The device in claim 3, including a guide cylinder (11) connected to the finger-like applicator (3), a cylinder cup (8) within said guide cylinder (11) and opening towards the spray nozzle (6), said cup connected to said piston and forming said actuating end (20) and extending coaxially with the piston (7).

5. The device of claim 4, wherein the locking mechanism includes a protrusion (21) on the cylinder cup (8) and a complementary groove (12, 13) on the inside of the guide cylinder (11).

6. The device in claim 5, wherein said groove is an annular groove on the inside of the guide cylinder (11) remote from the spray nozzle (6), said groove including a stop member (12) to prevent withdrawal of the piston (7) from the cylinder unit (1) of the applicator (3).

7. The device of claim 1, wherein the piston (7) moves intermittently, said outer actuating end (20) constructed and arranged at the end of the piston (7) remote from the spray nozzle (6) for establishing the intermittent movement in response to a selected force applied to said actuating end (20).

8. The device of claim 7, wherein the outer actuating end (20) includes a guide cylinder (15) connected to the finger-like applicator (3) and having stepped guide means (16) including a plurality of steps each having a guide (31), a cylinder cup (18) located in said guide cylinder and connected to said outer actuating end (20), said cup opening towards the spray nozzle (6) and extending coaxially with the piston (7), at least one radially extending projection (17) on the cylinder cup (18) engaging said stepped guide means (16) including said guide (31), means for establishing piston movement and to discharge a selected dose of the media, said means comprising said cup, said guide cylinder, and said guide, wherein said cup is turned and axially moved relative to the guide cylinder (15) and said guide (31) of said guide means.

9. The device of claim 8, wherein said guide cylinder (15) has a cylinder wall, said stepped guide means (16) is configured as holes through the cylinder wall, an outer cover cylinder (14) extends over the guide cylinder (15), said cover cylinder (15) having a free peripheral edge (26) remote from the spray nozzle (6) and turned inward to define a stop element for preventing withdrawal of the cup (18) and thereby said piston (7) from said cylinder unit (1).

10. The device of claim 9, wherein said cylinder cup has an outer surface and includes circumferentially spaced division indicia (19) on said outer surface, said peripheral edge (26) includes a marking unit (27) aligned with said division indicia (19) on the outer surface of the cylinder cup (18) in response to said turning and moving said cup, and wherein the circumferential distance between the division indicia (19) corresponds to the circumferential pitch of the stepped guide means (16) and to the respective circumferential spacing between adjacent guide steps (31), respectively.

11. The device of claim 10, wherein said free peripheral edge of the cylinder cup (18) includes a knurled portion (28).

12. The device of claim 8, wherein each guide step (31) includes an axially extending portion and a detent member (32, 33) cooperating therewith for permitting application movement of the piston (7) while blocking return movement thereof.

13. The device of claim 1, having said outer actuating end (20) connected to said piston and a piston member in said cartridge and a radially projecting member (2) on the end of the finger-like applicator (3) remote from the spray nozzle (6), said projecting member adapted to support the user's index and middle fingers for actuation of the piston (7) by thumb pressure against the outer actuating end (20).

* * * * *